US011978228B2

(12) United States Patent
Munsey, Jr. et al.

(10) Patent No.: US 11,978,228 B2
(45) Date of Patent: May 7, 2024

(54) SYSTEMS AND METHODS FOR DETERMINING AN ORIENTATION OF AN IMAGE

(71) Applicant: Ki Mobility LLC, Stevens Point, WI (US)

(72) Inventors: Douglas H. Munsey, Jr., Stevens Point, WI (US); Daniel H. Packard, Stevens Point, WI (US); Thomas J. Whelan, Stevens Point, WI (US); Patrick Abadi, Surrey (CA); William G. N. Coon, Longmont, CO (US); Robin D. Knight, Montreal (CA); Kimberly M. Wheeler, Montreal (CA)

(73) Assignee: KI MOBILITY LLC, Stevens Point, WI (US)

( * ) Notice: Subject to any disclaimer, the term of this patent is extended or adjusted under 35 U.S.C. 154(b) by 400 days.

(21) Appl. No.: 17/297,813

(22) PCT Filed: Nov. 21, 2019

(86) PCT No.: PCT/US2019/062635
§ 371 (c)(1),
(2) Date: May 27, 2021

(87) PCT Pub. No.: WO2020/112492
PCT Pub. Date: Jun. 4, 2020

(65) Prior Publication Data
US 2022/0036578 A1 Feb. 3, 2022

Related U.S. Application Data

(60) Provisional application No. 62/773,600, filed on Nov. 30, 2018.

(51) Int. Cl.
G06T 7/70 (2017.01)
G06T 7/62 (2017.01)
G06T 17/20 (2006.01)

(52) U.S. Cl.
CPC ............... *G06T 7/70* (2017.01); *G06T 7/62* (2017.01); *G06T 17/20* (2013.01)

(58) Field of Classification Search
CPC .... G06T 7/70; G06T 7/62; G06T 7/75; G06T 7/77; G06T 7/80; G06T 17/20;
(Continued)

(56) References Cited

U.S. PATENT DOCUMENTS

2008/0063294 A1\* 3/2008 Burt .................. H04N 23/6811
348/E5.079
2014/0085429 A1 3/2014 Hébert et al.

FOREIGN PATENT DOCUMENTS

WO 2020112492 A1 6/2020

OTHER PUBLICATIONS

Ichikari R, Onishi M, Kurata T. Fitting simulation based on mobile body scanning for wheelchair users. Journal on Technology and Persons with Disabilities. Mar. 2018. (Year: 2081).\*
Lemaire E, Lee W, Malric F, Robichaud M, Desrosiers MM. Real-time free-viewpoint 3D video for wheelchair seating assessment: preliminary assessment for local and remote applications. InIEEE International Workshop on Haptic Audio Visual Environments and their Applications Oct. 1, 2005 (pp. 4-pp). IEEE. (Year: 2005).\*
(Continued)

*Primary Examiner* — Edward F Urban
*Assistant Examiner* — Wassim Mahrouka
(74) *Attorney, Agent, or Firm* — Faegre Drinker Biddle & Reath LLP

(57) ABSTRACT

Embodiments for determining an orientation of a scanned image. In an exemplary embodiment, a method comprises receiving image data of an image of one or more objects. Each object of the one or more objects in the image includes a plurality of points on a surface of the object. The method further comprises generating a plurality of subsets of points of the plurality of points and fitting a parametric model to
(Continued)

more than one subset of the plurality of subsets to generate a plurality of parametric models. Further, the method identifies a parametric model of the plurality of parametric models that includes the largest number of points and orients the image based on the parametric model that includes the largest number of points.

23 Claims, 5 Drawing Sheets

(58) Field of Classification Search
CPC . G06T 2207/10012; G06T 2207/10024; G06T 2207/10028; G06T 2207/20076; G06T 2207/20081; G06T 2207/20101; G06T 2207/20116; G06T 2207/30196; G06T 2207/30244; A61B 5/1116; A61B 5/1128; A61B 5/1114
See application file for complete search history.

(56) References Cited

OTHER PUBLICATIONS

Azam et al., "Object Modeling from 3D Point Cloud Data for Self-Driving Vehicles," 2018 IEEE Intelligent Vehicles Symposium (IV), Jun. 26, 2018, pp. 409-414.

International Preliminary Report on Patentability received for PCT Patent Application No. PCT/US2019/062635, mailed on Feb. 18, 2021, 9 pages.

International Search Report and Written Opinion received for PCT Patent Application No. PCT/US2019/062635, mailed on Feb. 18, 2020, 11 pages.

Jaynes, Christopher, "View Alignment of Aerial and Terrestrial Imagery in Urban Environments," Lecture Notes in Computer Science, vol. 1737, Jan. 1, 1999, pp. 3-19.

* cited by examiner

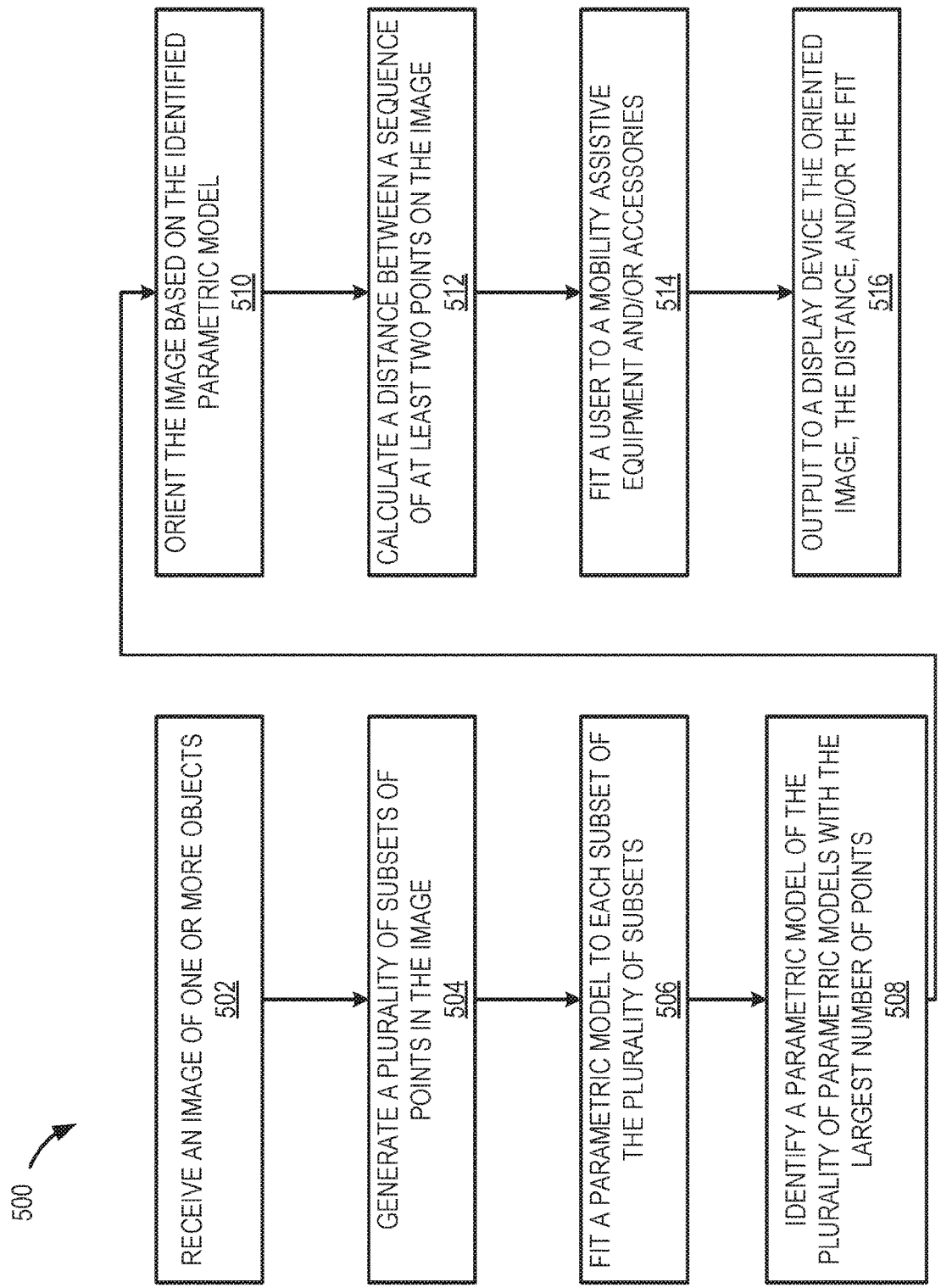

SYSTEMS AND METHODS FOR DETERMINING AN ORIENTATION OF AN IMAGE

CROSS REFERENCE TO RELATED APPLICATIONS

This application is a national stage application of PCT Application No. PCT/US2019/062635, internationally filed Nov. 21, 2019, which claims priority to U.S. Provisional Patent Application No. 62/773,600, filed Nov. 30, 2018, both of which are incorporated herein their entirety.

TECHNICAL FIELD

The present disclosure relates to automatically orienting a scanned image.

BACKGROUND

Subjects having mobility issues may seek advice from a medical professional to alleviate their mobility issues. A medical professional may prescribe assistive equipment to aid the subject's movement. Once the subject obtains a prescription, he/she will see a professional, such as assistant technology professional (ATP), to be fitted to the prescribed assistive equipment. The professional will measure, using a measuring tape, different parts of the subject to determine the appropriate size assistive equipment for the subject.

SUMMARY

Embodiments disclosed herein may automatically determine an orientation of an image. In at least some embodiments, determining the orientation of an imaged scene can reduce some of the errors associated with conventional embodiments for fitting a subject to mobility assistive equipment and increase efficiency for fitting a subject to mobility assistive equipment. Examples embodiments are as follows.

In an Example 1, a method for determining orientation of a scanned image, comprises: receiving image data of a scanned image of one or more objects, wherein each object of the one or more objects in the image includes a plurality of points on a surface of the object; generating a plurality of subsets of points of the plurality of points; fitting a parametric model to more than one subset of the plurality of subsets to generate a plurality of parametric models; identifying a parametric model of the plurality of parametric models that includes the largest number of points; and orientating the image based on the parametric model that includes the largest number of points.

In an Example 2, the method of Example 1, wherein orienting the image comprises setting the parametric model that includes the largest number of points as a ground of the image.

In an Example 3, the method of any one of Examples 1-2, wherein fitting a parametric model to more than one subset of the plurality of subsets comprises fitting a parametric model to each subset of the plurality of subsets.

In an Example 4, the method of any one of Examples 1-3, wherein the image comprises at least one of: the subject and mobility assistive equipment.

In an Example 5, the method of any one of Examples 1-4, wherein the image is a scan of the one or more objects from a three-dimensional scanner.

In an Example 6, the method of any one of Examples 1-5, further comprising outputting to a display device the oriented image.

In an Example 7, the method of Example 6, further comprising: receiving an input sequence from an input device, the input sequence comprising a selection of a sequence of at least two points on the image; and determining a real-world distance by summing adjacent points of the input sequence.

In an Example 8, the method of Example 7, further comprising determining an angular relationship between two adjacent segments, wherein each adjacent segment of the two adjacent segments comprises two or more adjacent points of the input sequence.

In an Example 9, the method of any one of Examples 7-8, further comprising outputting an image of a custom component for the mobility assistive equipment based on the real-world distance.

In an Example 10, the method of Example 9, wherein the custom component is at least one of: a tray cutout, a helmet sizing, and a seat.

In an Example 11, the method of any one of Examples 7-10, further comprising determining a size of a mobility assistive equipment to fit the subject based on the real-world distance.

In an Example 12, the method of any one of Examples 7-11, wherein the real-world distance is a Euclidean distance or a contour distance.

In an Example 13, the method of Example 11, further comprising transmitting the determined size to a remote electronic device.

In an Example 14, a non-transitory computer readable medium having a computer program stored thereon for determining orientation of a scanned image, the computer program comprising instructions for causing one or more processors to: receive image data of an image of one or more objects, wherein each object of the one or more objects in the image includes a plurality of points on a surface of the object; generate a plurality of subsets of points of the plurality of points; fit a first parametric model to a first subset of the plurality of subsets; orient the image based on the parametric model when a number of points on the first parametric model is greater than or equal to a threshold; and fit a second parametric model to a second subset of the plurality of subsets when the number of points on the first parametric model is less than a threshold.

In an Example 15, the non-transitory computer readable medium of Example 14, wherein to orient the image, the computer program comprises instructions to set the first parametric model as a ground of the image.

In an Example 16, the non-transitory computer readable medium of any one of Examples 14-15, the computer program comprising instructions to assign coordinates to each point of the plurality of points.

In an Example 17, the non-transitory computer readable medium of any one of Examples 14-16, wherein the image comprises at least one of: the subject and mobility assistive equipment.

In an Example 18, the non-transitory computer readable medium of any one of Examples 14-17, wherein the image is a scan of the one or more objects from a three-dimensional scanner.

In an Example 19, the non-transitory computer readable medium of any one of Examples 14-18, the computer program comprising instructions to output to a display device the oriented image.

In an Example 20, the non-transitory computer readable medium of Example 19, the computer program comprising instructions to: receive an input from an input device, the input comprising at least two points on the image; and determine a real-world distance between the two points.

In an Example 21, the non-transitory computer readable medium of Example 20, the computer program comprising instructions to determine a size of a mobility assistive equipment to fit the subject based on the real-world distance.

In an Example 22, the non-transitory computer readable medium of any one of Examples 20-21, wherein the real-world distance is a Euclidean distance or a contour distance.

In an Example 23, the non-transitory computer readable medium of Example 21, the computer program comprising instructions to transmit the determined size to a remote electronic device.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 5 is an illustration of a flow diagram for determining an orientation of an image used for fitting a subject to mobility assistive equipment.

Figure 1:
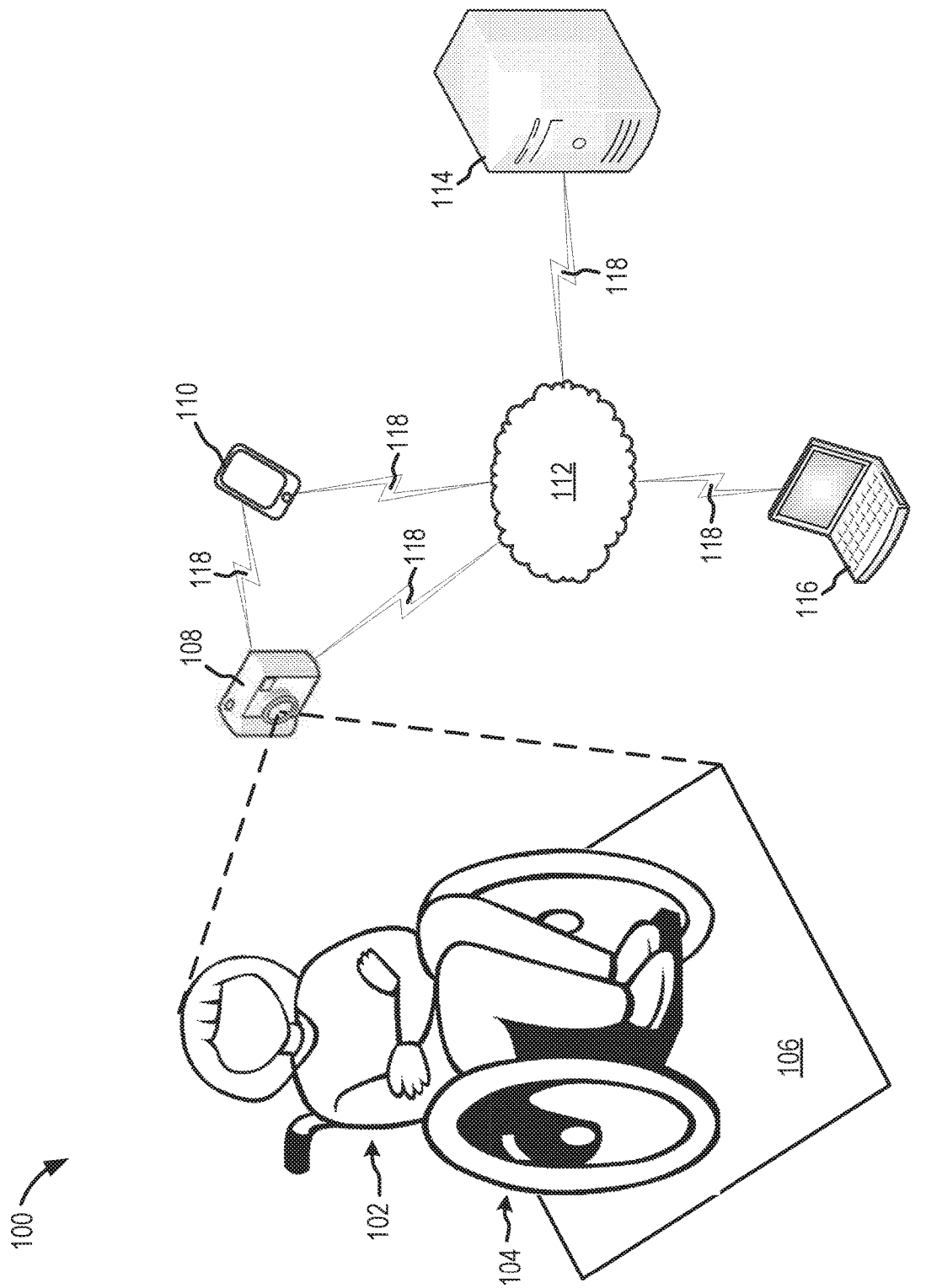
FIG. 1 is an illustration of an exemplary system for determining an orientation of an image.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

As stated above, to determine appropriately-sized assistive equipment, a subject may seek the advice of a professional, such as an ATP, who will then measure the subject using a measuring tape. This process can be very time consuming, susceptible to errors, and generally not reviewable by another professional. The embodiments disclosed herein may automatically determine an orientation of a scanned object, which can be used to alleviate some of these issues associated with fitting a subject to mobility assistive equipment. While the embodiments disclosed herein discuss using the automatic determination of a scanned object to fit a subject to mobility assistive equipment, the automatic determination of a scanned object may be used for any other suitable purpose.

FIG. 1 is an illustration of an exemplary system 100 for determining an orientation of an image. The exemplary system 100 includes a subject 102 arranged on mobility assistive equipment 104 located on the ground 106. While the system 100 depicts both a subject 102 and mobility assistive equipment 104, in other exemplary embodiments the system 100 may only include a subject 102 or mobility assistive equipment 104.

In the illustrated embodiment, the system 100 also includes a sensing device 108, a first electronic device 110, a network 112, a server 114, and a second electronic device 116. The sensing device 108 is configured to sense one or more objects. For example, the sensing device 108 is configured to sense the subject 102, the mobility assistive equipment 104, and/or the ground 106. In embodiments where only a subject 102 is present, then the sensing device 108 may only sense the subject 102, the ground 106, and/or other nearby objects. In embodiments where only the mobility assistive equipment 104 is present, the sensing device 108 may only image the mobility assistive equipment 104, the ground 106, and/or other nearby objects.

In embodiments, the sensing device 108 may be operated by the subject 102, a third-party, and/or be configured to image the subject 102 in response to a command provided via the network 112 by, for example, the server 114 and/or the second electronic device 116. In at least some embodiments, the sensing device 108 is operated to sense the one or more objects from one or more different viewpoints. For example, the sensing device 108 may be operated to sense the one or more objects in a scene from a 360-degree hemispherical view. Alternatively, the sensing device 108 may be operated to sense the one or more objects in a scene in less than a 360-degree hemispherical view. These viewpoints may be stitched together to form a 3D model of the one or more objects, as discussed in more detail below.

The sensing device 108 may be handheld or fixed. Additionally, the sensing device 108 may be one or a combination of a plurality of different types of sensors. Each of these sensors may be used to determine the depths of different points included in a sensed object. As such, for each pixel in an image sensed by the sensing device 108, the depth of the pixel may be known.

For example, the sensing device 108 may be a three-dimensional (3D) sensor (e.g., a phase-based laser scanner, time-of-flight scanner). A 3D sensor, such as a laser scanner or a time of flight scanner, emits a signal (e.g., a laser) which is reflected by an object. The 3D sensor receives the reflected signal and based on the phase shift or the time of flight of the signal, a depth of the point that reflects the signal can be calculated.

As another example, the sensing device 108 may be a stereo-depth sensor/multi-camera system. A stereo-depth sensor/multi-camera system senses two images of scene and a difference between the same points in both the images are used to determine the point's depth.

As even another example, the sensing device 108 may be an active monocular sensor. For an active monocular sensor, a pattern is projected onto a scene and the depths of points of objects in the scene are determined based on distortions in the pattern.

As yet another example, the sensing device 108 may be a monocular/photogrammetry sensor, and/or a passive monocular sensor. For a monocular/photogrammetry sensor, depth can be determined using techniques from photogrammetry. And, for a passive monocular sensor, a mosaic filter can be applied to a sensed image to compute depth information.

An advantage to using a fixed multi-sensor scanning system as the sensing device 108 is that only a single frame of the scene may need to be obtained. Another advantage of using the multi-sensor scanning system as the sensing device 108 is that the sensing device 108 may be calibrated so the images from the multi-sensor scanning system can be stitched together quickly due to the known spatial configuration of the multiple sensors relative to one another. An advantage of using a mechanical single-sensor scanning system as the sensing device 108 is that it's easier for a user performing the scan because the user doesn't have to walk around the subject 102. Another advantage of using a mechanical single-sensor scanning system as the sensing device 108 is that mechanical single-sensor scanning systems includes components (e.g., stepper motors, encoders, etc.) that allow for accurate estimates of sensor location. An advantage of using a handheld scanner as the sensing device 108 is that handheld scanning provides greater flexibility and portability. To facilitate alignment of images (discussed in more detail below), the handheld scanner can include components (e.g., inertial measurement units, visual odometry, etc.) to reduce the likelihood of misalignment of the images.

After the sensing device 108 senses one or more objects (e.g., the subject 102, the mobility assistive equipment 104, and/or the ground 106) in a scene, data of the sensed objects may be transferred by the sensing device 108 to the first electronic device 110 via a communication link 118. In response to receiving the sensed data, the first electronic device 110 may perform additional processing on the data to construct a 3D model of the sensed objects and determine the orientation of the 3D model. In some embodiments, the electronic device 110 can use the oriented 3D model to fit the subject 102 to mobility assistive equipment 104, other mobility assistive equipment not illustrated, and/or one or more accessories to mobility assistive equipment. Each of these functions is explained in more detail below.

Figure 2:
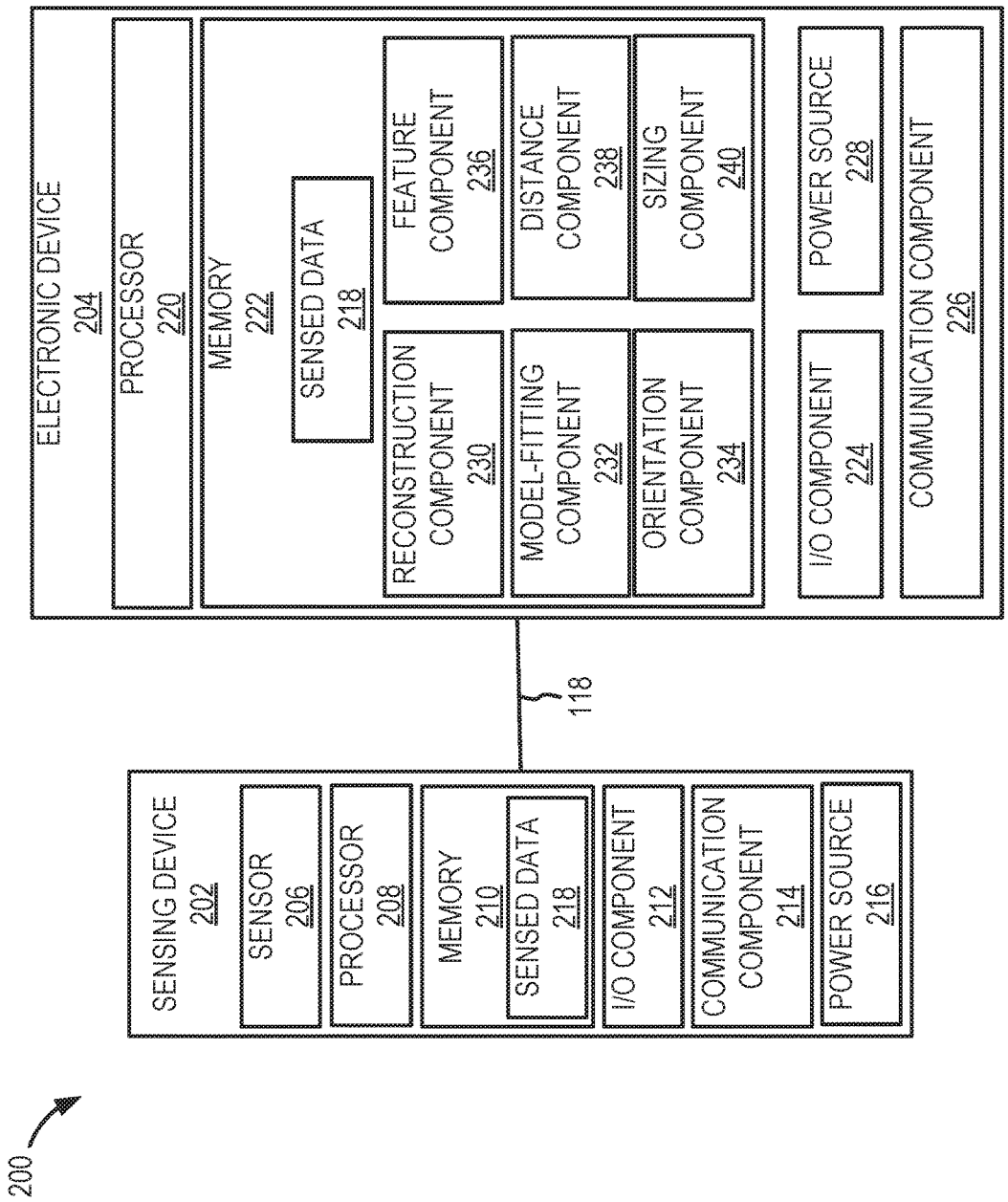
FIG. 2 is a block diagram depicting a sensing device and an electronic device included in the system of FIG. 1.

In the illustrated embodiment, the mobility assistive equipment 104 is a wheelchair. However, the mobility assistive equipment 104 may be other types of assistive equipment including, but not limited to, walkers, crutches, prosthetics, and/or the like. Furthermore, While the sensing device 108 is depicted as being separate from the first electronic device 110, in alternative embodiments, the sensing device 108 and the first electronic device 110 are included in the same device. In these embodiments, the sensing device 108 may perform additional processing on the data to construct a 3D model of the sensed objects and/or determine the orientation of the 3D model. In at least some embodiments, the sensing device 108 may use the orientation of the 3D model to fit the subject 102 to mobility assistive equipment 104 and/or other mobility assistive equipment not illustrated. Additionally, or alternatively, data of the sensed the subject 102, the mobility assistive equipment 104, and/or the ground 106, may be transferred by the sensing device 108 to the server 114 and/or the second electronic device 116 via a network 112 and communication links 118. In response, the server 114 and/or the second electronic device 116 may perform additional processing on the data to construct a 3D model of the sensed objects and/or determine the orientation of the 3D model. In at least some embodiments, the second electronic device 116 may use the 3D model to fit the subject 102 to mobility assistive equipment 104 and/or other mobility assistive equipment not illustrated. Exemplary components of the sensing device 108 and the first electronic device 110 and/or the second electronic device 116 are depicted in FIG. 2.

The network 112 may be any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. Additionally, or alternatively, the network 112 may include a combination of multiple networks, which may be wired and/or non-wired.

The communication links 118 may be, or include, a wired link (e.g., a link accomplished via a physical connection) and/or a wireless communication link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices and should not be understood to be limited to a direct, persistent, or otherwise limited communication channel. That is, according to embodiments, the communication link 118 may be a persistent communication link, an intermittent communication link, an ad-hoc communication link, and/or the like. The communication link 118 may refer to direct communications between the components of the system 100, and/or indirect communications that travel between the components of the system 100 via at least one other device (e.g., a repeater, router, hub, and/or the like). The communication link 118 may facilitate uni-directional and/or bi-directional communication between the components of the system 100. Data and/or control signals may be transmitted between the components of the system 100 to coordinate the functions of the components of the system 100. In embodiments, data of the sensed subject 102, mobility assistive device 104 and/or ground 106 may be downloaded by the first electronic device 110, the server 114 and/or the second electronic device 116 periodically or on command. An ATP (not shown), clinician (not shown) and/or the subject 102 may communicate with the components of the system 100, for example, to acquire image data of the image of the subject 102, the mobility assistive device 104 and/or the ground 106.

In embodiments, the first electronic device 110 and/or the second electronic device 116 is accessible by an ATP and/or clinician to review the 3D model of the subject 102, the mobility assistive device 104 and/or the ground 106. In the event the second electronic device 116 is used by an ATP and/or clinician to review the 3D model, the review may be transmitted to the first electronic device 110 by the second electronic device 116 via the network 112 and a communication link 118 so the review can be received by the subject 102. Additionally, or alternatively, the ATP and/or the clinician may also send, via the network 112 and a communication link 118, a recommendation as to an appropriately-sized mobility assistive equipment 104 for the subject 102 and/or other mobility assistive not depicted upon reviewing the 3D model. In at least some embodiments, the review of the 3D model and/or the recommendation can be transmitted by the first electronic device 110 and/or the second electronic device 116 to the server 114 for storage and/or analysis.

The illustrative system 100 shown in FIG. 1 is not intended to suggest any limitation as to the scope of use or functionality of embodiments of the present disclosure. The illustrative system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are within the ambit of the subject matter disclosed herein.

FIG. 2 is a block diagram 200 depicting a sensing device 202 and an electronic device 204 included in the system of FIG. 1. In the illustrated embodiment, the sensing device 202 includes a sensor 206, a processor 208, memory 210, an I/O component 212, a communication component 214, and a power source 216.

The sensing device 206 is configured to sense one or more objects in a scene (e.g., subject 102, the mobility assistive equipment 104, and/or the ground 106). The sensed objects may then be used to construct a 3D model of the one or more objects, as explained below. The data sensed by the sensor 206 may be saved as sensed data 218 in memory 210. As stated above, exemplary sensing devices 206 include, but are not limited to, (3D) sensors, stereo-depth sensor/multi-camera systems, active monocular sensors, monocular/photogrammetry sensors, and/or passive monocular sensors. Each of these sensing devices 206 may provide sensed data 218 that includes depth information and color data for different points on objects within a scene. Stated another way, the sensing device 206 can produce an image where depth and color information are known for each pixel in the image.

The sensed data 218 may then be transferred by the sensing device 202 to the electronic device 204 via a communication link 118 for further processing, including, for example, determining a 3D model using the sensed data 218 and/or determining the orientation of an image. In at least some embodiments, the electronic device 204 may use the 3D model to fit a subject 102 to mobility assistive equipment, as explained in more detail below. While the functions discussed above are discussed in relation to the sensing device 202, one or more of those functions may be performed by the electronic device 204. Additionally, or alternatively, one or more functions of the electronic device 204 discussed below may be performed by the sensing device 202.

The processor 208 may include, for example, one or more processing units, one or more pulse generators, one or more controllers, one or more microcontrollers, and/or the like. The processor 208 may be any arrangement of electronic circuits, electronic components, processors, program components and/or the like configured to store and/or execute programming instructions, to direct the operation of the other functional components of the sensing device 202, to perform processing on any sensed data 218, instruct the communication component 214 to transmit data and/or receive data, and may be implemented, for example, in the form of any combination of hardware, software, and/or firmware.

In embodiments, the processor 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processor 208 may include a processing unit configured to communicate with memory 210 to execute computer-executable instructions stored in the memory 210. As indicated above, although the processor 208 is referred to herein in the singular, the processor 208 may be implemented in multiple instances, distributed across multiple sensing devices, instantiated within multiple virtual machines, and/or the like.

The processor 208 may also be configured to store information in the memory 210 and/or access information from the memory 210. For example, the processor 208 may be configured to store sensed data 218 sensed by the sensor 206 in memory 210. The sensed data 218 may include any of the data sensed by the sensor 206 as discussed above. Additionally, or alternatively, the sensed data 218 may include one or more locations and/or device parameters. Device parameters may include any number of different parameters associated with a state of the sensor 206 and/or any other device (e.g., the electronic device 204) and may include, for example, battery life, end-of-life indicators, processing metrics, motion parameters of the electronic device 204 and/or the like. Additionally, or alternatively, location data indicative of the location of the sensing device 202 and sensor 206 may be saved as sensed data 218. As stated above, the sensed data 218 may be used to determine the orientation of the image. In at least some embodiments, the orientation of the image may facilitate fitting a subject 102 to mobility assistive equipment 104 as discussed in more detail below.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

Computer-executable instructions stored on memory 210 may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all the functionality contemplated herein may also, or alternatively, be implemented in hardware and/or firmware.

The I/O component 212 may include a user interface configured to present information to a user or receive an indication from a user. For example, the I/O component 212 may include and/or be coupled to a display device, a printing device, a light emitting diode (LED), and/or the like, and/or an input component such as, for example, a button, a joystick, a satellite dish, a scanner, a printer, a wireless device, a keyboard, a pen, a voice input device, a touch input device, a touch-screen device, an interactive display device, a mouse, and/or the like. In embodiments, the I/O component 212 may be used to present and/or provide an indication of any of the data sensed and/or produced by the sensing device 202 and/or any other components depicted in FIGS. 1 and 2. Additionally, or alternatively, the I/O component 212 may receive a command from a subject 102 and/or third party and, in response to the command, the processor 208 may execute the command. For example, the processor 208 may instruct the sensor 206 to image one or more objects in response to a corresponding command.

The communication component 214 may be configured to communicate (i.e., send and/or receive signals) with the electronic device 204 and/or other devices included in FIGS. 1 and 2 (e.g., the first electronic device 110, the server 114, and/or the second electronic device 116). For example, the communication component 214 may be configured to receive sensed data 218 from the sensor 206 and/or memory 210 and/or send the sensed data 218 to the electronic device 204. The communication component 214 may include, for example, circuits, program components, and one or more transmitters and/or receivers for communicating wirelessly with one or more other devices such as, for example, the electronic device 204. According to various embodiments, the communication component 214 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 212 may include any combination of hardware, software, and/or firmware configured to facilitate establishing, maintaining, and using any number of communication links.

The power source 216 provides electrical power to the other operative components of the sensing device 202 (e.g., the sensor 206, the processor 208, the memory 210, the I/O component 212, and/or the communication component 214), and may be any type of power source suitable for providing the desired performance and/or longevity requirements of the sensing device 202. In various embodiments, the power source 216 may include one or more batteries, which may be rechargeable (e.g., using an external energy source). The power source 216 may include one or more capacitors, energy conversion mechanisms, and/or the like.

In the illustrated embodiment, the electronic device 204 includes a processor 220, memory 222, an I/O component 224, a communication component 226, and a power source 228. The electronic device 204 may be used as the first electronic device 110 and/or the second electronic device 116. As such, the components included in the electronic device 204 may be included in the first electronic device 110 and/or the second electronic device 116. Additionally, or alternatively, some or all the components of the electronic device 204 may be incorporated into the server 114. Furthermore, while the illustrated embodiments depict the electronic device 204 as including the aforementioned components, one or more of those components may be included in the sensing device 202.

The processor 220 may include, for example, one or more processing units, one or more pulse generators, one or more controllers, one or more microcontrollers, and/or the like. The processor 220 may be any arrangement of electronic circuits, electronic components, processors, program components and/or the like configured to store and/or execute programming instructions, to direct the operation of the other functional components of the electronic device 204 and may be implemented, for example, in the form of any combination of hardware, software, and/or firmware.

In embodiments, the processor 220 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processor 220 may include a processing unit configured to communicate with memory 222 to execute computer-executable instructions stored in the memory 222. As indicated above, although the processor 220 is referred to herein in the singular, the processor 220 may be implemented in multiple instances, distributed across multiple sensing devices, instantiated within multiple virtual machines, and/or the like.

The processor 220 may be configured to store information in the memory 222 and/or access information from the memory 222. For example, the processor 220 may be configured to store sensed data 218 received from the sensing device 202. The sensed data 218 may be used by the processor 220 to determine the orientation of the image corresponding to the sensed data 218. In at least some embodiments, the processor may use the orientation of the image to fit a subject 102 to mobility assistive equipment 104.

In embodiments, the memory 222 may include a reconstruction component 230, a model-fitting component 232, an orientation component 234, a distance component 238, and/or a sizing component 240. While the reconstruction component 230, the model-fitting component 232, the orientation component 234, the distance component 238, and the sizing component 240 are depicted as being included in the memory 222, the reconstruction component 230, the model-fitting component 232, the orientation component 234, the distance component 238, and the sizing component 240 may be included in the memory 210 and executed by the processor 208. Additionally, or alternatively, the reconstruction component 230, the model-fitting component 232, the orientation component 234, the distance component 238, and the sizing component 240 may be included in memory of the server 114 and executed by a processor of the server 114.

As stated above, the sensed data 218 may include depth information and color information for different pixels included in an image produced by the sensing device 202. In embodiments, the reconstruction component 230 processes the sensed data 218 to form a 3D model of the scene sensed by the sensing device 202. To form a 3D model of the scene, the reconstruction component 230 converts the sensed data 218 to 3D data and aligns the images. In embodiments, the sensed data 218 may be augmented with additional sensor data, e.g., inertial measurement unit data, which may be referred to as "Inertial Odometry" or "6 Degree of Freedom (DOF) Pose Estimation" to facilitate the reconstruction component 230 converting the sensed data 218 to 3D data and aligning the image.

To convert the sensed data 218 to 3D data, the reconstruction component 230 may register the pixels in the different images produced by the sensing device 202 to each other. By registering pixels in different images, the 3D model created by the reconstruction component 230 may include color definition. Additionally, or alternatively, the reconstruction component 230 may convert information about each pixel into real-world 3D coordinates. For example, the reconstruction component 230 may apply a transformation function to each pixel to convert the information about a pixel (e.g., $A_{nm}$, $D_{nm}$, where $D_{nm}$ is the depth of pixel $A_{nm}$) into real-world 3D coordinates (e.g., x, y, z coordinates).

To align the images to produce a point-cloud representation, the reconstruction component 230 may use, for example, one or more of the following types of algorithms: an iterative closest point (ICP) matching algorithm, a fastglobal registration algorithm, a fast-point feature histogram (FPFH) algorithm, graph optimization, bundle adjustment, keypoint registration, and signed distance functions (SDFs). However, these are only examples and not meant to be limiting.

In at least one example, the reconstruction component 230 uses the real-world coordinates of pixels in the first image in a sequence of images produced by the sensing device 202 as a base for the global 3D point-cloud representation. The reconstruction component 230 may then define the real-world coordinates of the pixels in subsequent images relative to the real-world coordinates of pixels in the first image. In another example, the reconstruction component 230 uses the real-world coordinates of pixels in the last image in a sequence of images produced by the sensing device 202 as a base for the global 3D point-cloud representation. The reconstruction component 230 may then define the real-world coordinates of the pixels in prior images relative to the real-world coordinates of the pixels in the last image.

As stated above, each individual image sensed by the sensing device 202 may be taken from the same viewpoint or from different viewpoints. As such, there may be overlap between the images. To reduce the computational requirements during alignment of the images and subsequent operations performed by the electronic device 204, the reconstruction component 230 may remove duplicate or near duplicate data captures in the different images.

Once aligned, the reconstruction component 230 has created a 3D point-cloud representation of the scene. Stated another way, each non-overlapping pixel in the images produced by the sensing device 202 has a real-world coordinate assigned to it and they collectively form a point-cloud representation of the scene. The point-cloud representation may be saved as sensed data 218.

In at least some embodiments, the reconstruction component 230 can fit one or more surfaces onto the point cloud representation. For example, in an exemplary embodiment, the reconstruction component 230 can generate and fit a set of polygons (e.g., triangles constructed via Delaunay triangulation) to the point cloud representation to generate a mesh. An advantage of the mesh is that the exact 3D coordinates of the point cloud representation are maintained. As another example, the reconstruction component 230 can generate a parametric model corresponding to surfaces of the point cloud representation. However, unlike creating a mesh, the parametric model does not preserve exact 3D coordinates of the original point cloud.

Additionally, or alternatively, the reconstruction component 230 can generate a Solid Model of the surfaces determined by the reconstruction component 230. The Solid Model includes closed surfaces and can be used by computer-aided drafting software to manipulate model aspects of the model (e.g., separate the subject 102 from the mobility assistive equipment 104 in the image (e.g., the image 300 and/or the image 400).

In embodiments where a monocular camera is used as the scanning device 108, the reconstruction component 230 may identify correspondences between identified features of the image. (Features of the image can be identified by the feature component 236 as discussed below.) Further, the reconstruction component 230 can apply generalizations of stereo block matching to infer 3D coordinates for various features and pixels in the image. In embodiments, the 3D coordinates are reconstructed incrementally by combining information from the sequence of images.

The point-cloud representation is disclosed below in relation to various other functions performed by the electronic device 204, however, the mesh, parametric model, the Solid Model, and/or the reconstructed 3D coordinates may be used by the electronic device 204 in performance of those various functions.

As stated above, the sensed data 218 may include a point cloud representation of a scene imaged by the sensing device 202. As such, each point of the point cloud may include corresponding coordinates included in the sensed data 218. Using this data stored as sensed data 218, the model-fitting component 232 may fit one or more of the points included in the point cloud representation of the image to a plurality of parametric models. To do so, the model-fitting component may use a Random Sample Consensus model (RANSAC).

For example, the model-fitting component 232 may randomly select points of the plurality of points included in the point cloud representation to generate one or more subsets of points of the plurality of points included in the point cloud representation. The generated subsets of points may include the same number of points as each other or a different number of points. For a subset of points, the model-fitting component 232 determines a parametric model that can be fitted to the largest number of points included in the subset of points. To do so, the model-fitting component 232 may use a cost function minimization method where the cost may be represented by the mean square error (MSE), Cauchy loss function, Huber loss function, or any number of other robust loss function alternatives.

Additionally, or alternatively, the model-fitting component 232 may determine the parametric model having the largest number of points using an iterative process. For example, an initial estimate of the parametric model may be determined from RANSAC and the estimate improved upon by applying small transformations to the current best fit to achieve a closer fit.

While the embodiments disclosed herein are primarily discussed in relation to determining the parametric model having the largest number of points, which is in turn used to determine a ground plane, the model-fitting component 232 may additionally, or alternatively, determine the parametric model having a specific diameters, cambers, separations, 6 degrees of freedom pose, etc., which can be used to determine wheels of a wheel chair in the image. As another example, the model-fitting component 232 may determine parametric model having a specific radius and/or position, which can be used to determine spheres in the image. As even another example, the model-fitting component 232 may determine parametric model having a specific complex form that is, for example, modeled using a CAD program, and parametrized by physical characteristics (e.g., shoulder width), which can be used to determine biological features in the image. All of these examples are considered to be within the ambit of this disclosure.

After fitting one or more points of the subset of points to a parametric model, the model-fitting component 232 may determine whether the number of points fitted to the parametric model satisfies a threshold. For example, the model-fitting component 232 may set a threshold at N points and if a parametric model fitted to one or more points of the subset of points includes N or more points, then the model-fitting component 232 may send that data to the orientation component 234. Alternatively, if the parametric model does not include N or more points, then the model-fitting component 232 may generate a new subset of points of the plurality points included in the point cloud representation. This process may be repeated until the model-fitting component 232 is able to fit a parametric model to a subset of points such that the parametric model includes N or more points of the subset of points.

In at least one other embodiment, the model-fitting component 232 may generate a predetermined number of subset of points of the plurality points included in the point-cloud representation. For example, the model-fitting component 232 may generate M subsets of points. And, for the subsets $m_n$ of M, the model-fitting component 232 may determine the subset of M including the largest number of points that can be fitted to a parametric model. For example, for the subset $m_0$ of M, the model-fitting component 232 may determine the largest number of points of $m_0$ that can be fitted to a parametric model. Then, for the subset $m_1$ of M, the model-fitting component 232 may determine the largest number of points of $m_1$ that can be fitted to a parametric model. If the number of points of mi fitted to a parametric model is larger than the number of points of $m_0$ fitted to a parametric model, then the subset $m_0$ is disregarded. And, the next subset $m_2$ of M is compared to $m_1$. That is, the number of points of the subset $m_2$ fitted to parametric model is compared against the number of points of $m_1$ fitted to a parametric model and the subset with the fewer number of points fitted to a parametric model is disregarded. This process is continued until all the subsets of M are analyzed and the subset of M with the largest number of points fitted to a parametric model is determined. The subset of M with the largest number of points fitted to a parametric model is used to orient an image, as discussed below. In at least some embodiments, the subset of M with the largest number of points fitted to a parametric model may also be sent to and used by the orientation component 234, as set forth below.

Figure 3:
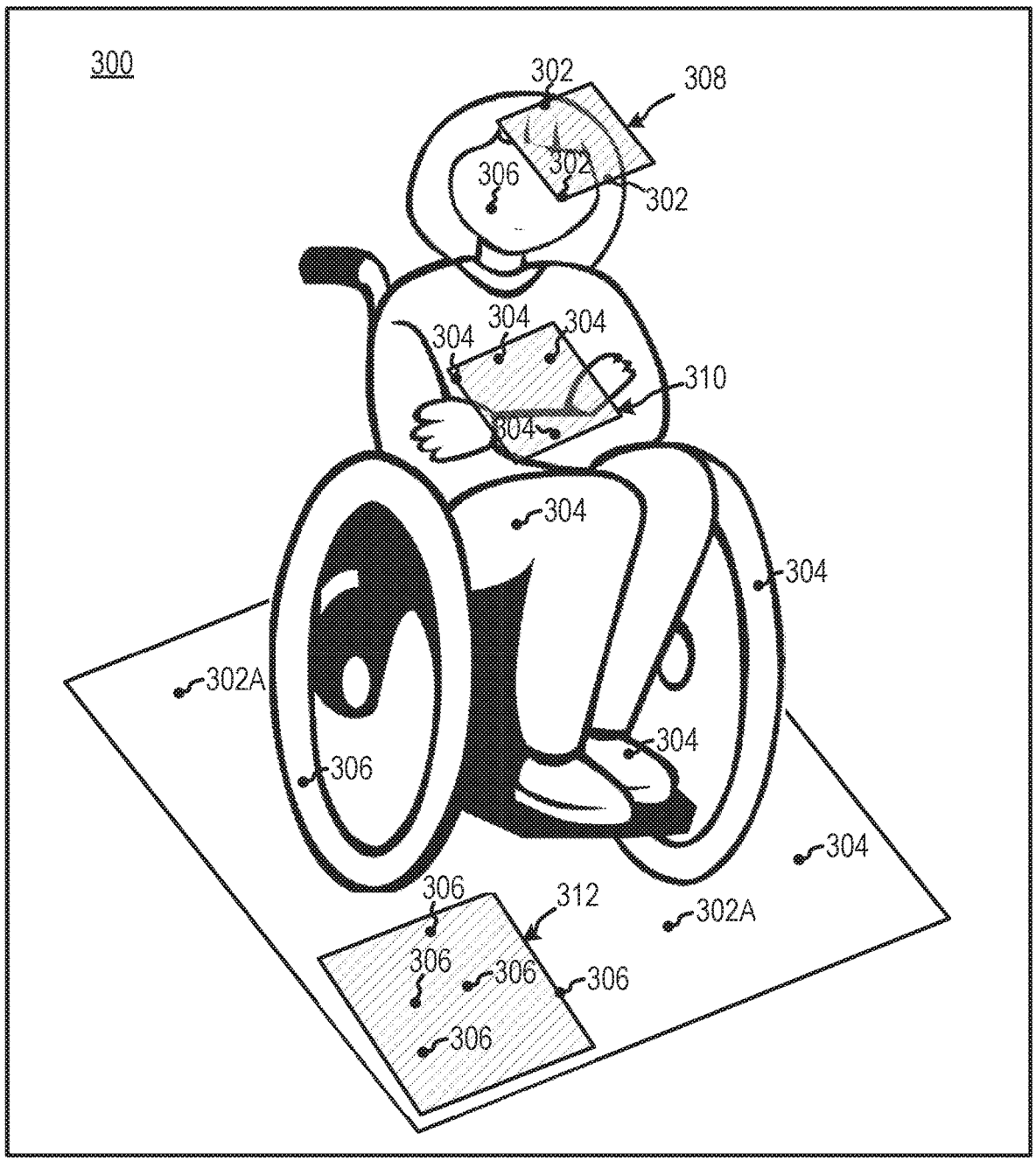
FIG. 3 is an illustration of an exemplary image for which an orientation is determined.

FIG. 3 is an illustration of an exemplary image 300 for which a model-fitting is performed by the model-fitting component 232. In the illustrated embodiment, the model-fitting component 232 randomly generated three subsets of points 302, 304, 306 from the point-cloud representation of the image 300. Further, the model-fitting component 232 has fitted a respective parametric model 308, 310, 312 to each subset of points 302, 304, 306, such that each of the parametric models 308, 310, 312 passes through the largest number of points possible in each respective subset of points 302, 304, 306. For example, the parametric model 308 includes the largest number of points of the subset of points 302 that the parametric model 308 can pass through. That is, the points 302A do not lie on the parametric model 308. Similar parametric models 310, 312 have been generated for the subsets of points 304, 306, respectively.

In at least one embodiment, once the parametric models 308, 310, 312 are generated, the model-fitting component 232 determines which parametric model of the parametric models 308, 310, 312 includes the largest number of points. In this example, the parametric model 312 includes the largest number of points lying on the parametric model 312. In the event no more subsets of points are being generated by the model-fitting component 232 and/or the number of points included in the parametric model 312 is greater than or equal to a threshold, data of the parametric model 312 may be sent to the orientation component 234. In at least some embodiments, the subsets of points 302, 304, 306 may be generated sequentially to determine whether a point is included in a parametric model fitted to the one of the subsets of points 302, 304, 306 satisfies a threshold and, therefore, no more subsets of points 302, 304, 306 need to be generated.

After the orientation component 234 receives data corresponding to a parametric model (e.g., one of the parametric models 308, 310, 312) including the largest number of points from the model-fitting component 232, the orientation component 234 can determine the orientation of the image 300. For example, the orientation component 234 can orient the image 300 so that the parametric model including the largest number of points is arranged on the bottom of the image 300. The reason being is because the parametric model including the largest number of points will likely be the ground and/or floor captured in the image 300 due to the ground and/or floor having the largest number of points on the same parametric model relative to other objects (e.g., the subject 102, mobility assistive device 104, etc.) included in the image 300. As such, the orientation component 234 may set the parametric model including the largest number of points as the ground and/or floor, which will result in the correct orientation of the image 300. Based on the ground plane being identified, the orientation component 234 can define the z-axis as being normal to the ground plane with the positive z-direction being identified as the direction in which the center of mass of the image is located. In embodiments, the orientation component 234 can also define the z-axis as being the upward direction in the image.

Orienting the image 300 in this manner provides benefits over other embodiments. For example, a landmark may be used to orient an image. However, in circumstances where the landmark is not present, the image may not be able to be oriented and/or may need to be oriented by a human. Without being able to orient the image and/or orientation performed by a human, which may be performed inaccurately, one or more processes performed using the image (e.g., fitting a subject 102 to mobility assistive equipment 104) may be performed inaccurately. The embodiments disclosed herein reduce the likelihood of this issue occurring.

In at least some embodiments, the memory 222 (depicted in FIG. 2) includes a feature component 236. The feature component 236 may determine one or more features in the image 300 using, for example, scale-feature invariant transform (SIFT) algorithm, speeded up robust features (SURF) algorithm, a FPFH algorithm, and/or the like. In embodiments, the feature component 236 may determine the subject 102 and the mobility assistive equipment 104 in an image 100. Additionally, or alternatively, the feature component 236 may determine specific features of the subject 102 and/or the mobility assistive equipment 104. For example, the feature component 236 may identify the head, appendages, a torso, joints of the subject 102 and the mobility assistive equipment 104, and/or the like. In at least some embodiments, the feature component 236 may be facilitated by a user of the electronic device 204. For example, a user can annotate portions (e.g., the subject 102, mobility assistive equipment 104, specific features of the subject 102) of the image 100 that can be stored in memory 222 as features. Additionally, or alternatively, a scan of the mobility assistive equipment 104 without the subject 102 may be obtained, which can facilitate separating the subject 102 from the mobility assistive equipment 104 by identifying what the exclusive features of the mobility assistive equipment 104.

By determining the subject 102 and the mobility assistive equipment 104, a user of the electronic device 204 may separate the subject 102 form the mobility assistive equipment 104. In at least some embodiments, a user of the electronic device 204 may facilitate separation of the subject 102 from the mobility assistive equipment 104 by identifying parametric models and/or contours along which the separation of the subject 102 and the mobility assistive equipment 104 should be performed.

By identifying features of the subject 102 and the mobility assistive equipment 104, the feature component 236 can identify a plane of maximal symmetry by comparing the identified features and/or determining and analyzing the moment of inertia of the identified subject 102 and/or mobility assistive equipment 104. The feature component 236 can then identify the plane having maximal symmetry as the sagittal plane. In at least some embodiments, the feature component 236 can store the plane in memory 222, use the plane to identify the front, right, left and/or back in the image, and/or use the plane to facilitate fitting the subject 102 to the mobility assistive equipment (discussed below).

By identifying features of the subject 102, the feature component 236 can determine asymmetries of the subject 102. For example, the feature component 236 can whether the subject 102 has windswept knee, scoliosis, etc. Then, when fitting the subject 102 to the mobility assistive equipment 104, as explained in more detail below, the asymmetries of the subject 102 can be considered to determine a better fit for the subject 102 than if the asymmetries of the subject 102 weren't considered. Additionally, or alternatively, identifying asymmetries may allow the subject 102 to receive specific reimbursements for the mobility assistive equipment 104.

By identifying the joints of the subject 102 and/or the mobility assistive equipment 104, the feature component 236 may be configured to articulate the joints using, for example, a skeletal tracking software, which can help determine the functional reach of the subject 102. When articulating the joints, the angular limits of joints of the subject 102 and/or the mobility assistive equipment 104 may be predefined and/or configured by a user of the electronic device 204. Once the angular limits of the joints of the subject 102 and the mobility assistive equipment 104 are set, the limits may be input into a forward kinematics system, which can be sampled for various combinations of joint angles to visualize the volume that can be assessed by the subject 102. In at least some embodiments, the position of the subject 102 relative to the mobility assistive equipment 104 in the image can be adjusted. For example, the hip posture of the subject 102 may be adjusted in the image, which can have repercussions on the functional reach of the subject 102. The feature component 236 can save the functional reach of the subject 102 in memory 222.

In embodiments where the mobility assistive equipment 104 is a wheelchair, the feature component 236 can determine the subject's 102s wheel access and stroke using the functional reach model of the subject 102. The electronic device 204 using the identified features of the feature component 236 can account for obstacles to the subject's 102 functional reach that may limit the subject's 102 functional reach such as the lateral position of the wheelchair's wheels relative to the wheelchair's armrests.

Additionally, or alternatively to the embodiments set forth above, the memory 222 (depicted in FIG. 2) may include a distance component 238 (depicted in FIG. 2). The distance component 238 may be configured to determine a distance between points included in an image (e.g., image 300 and/or image 400 depicted in FIG. 4).

Figure 4:
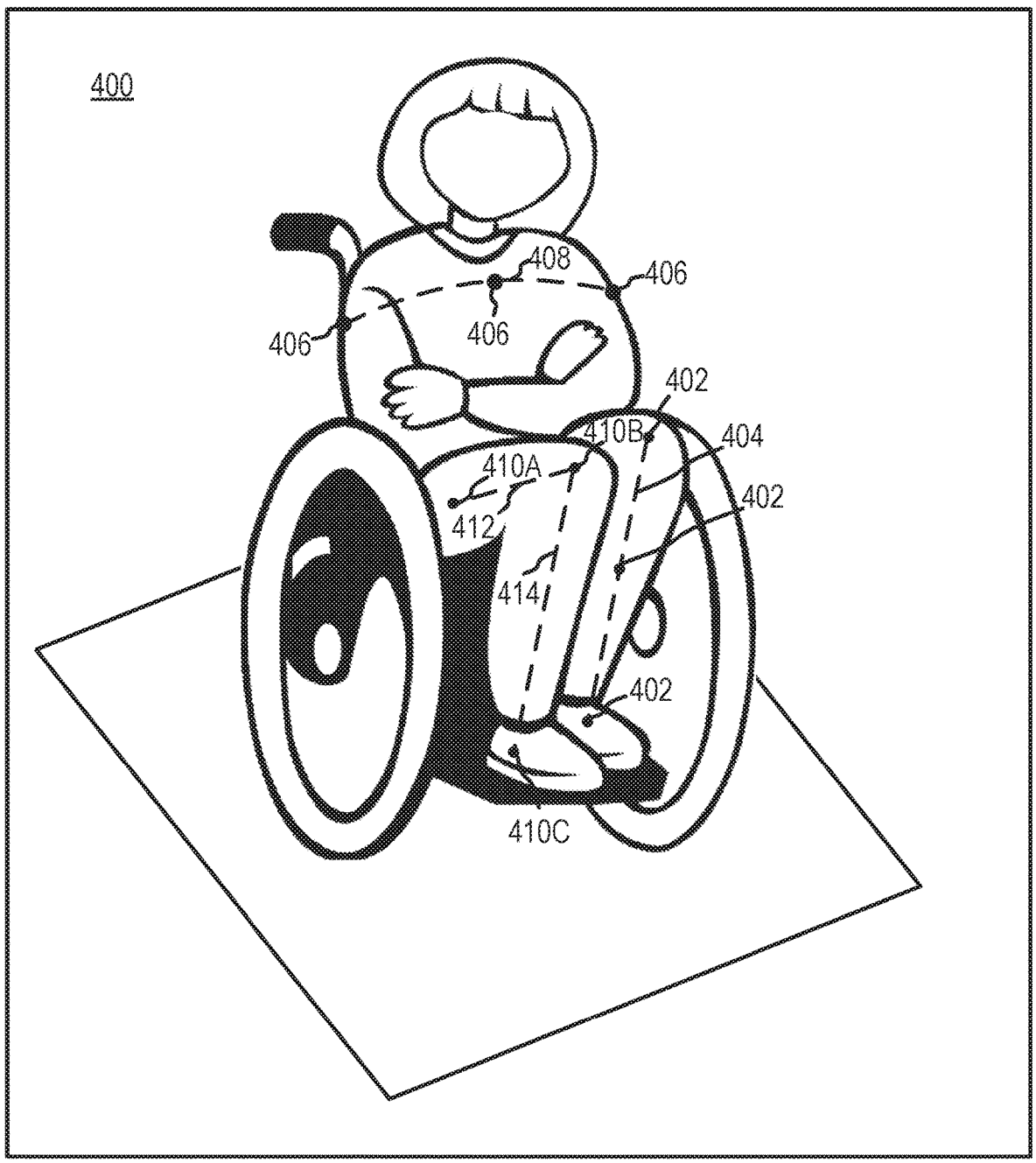
FIG. 4 is an illustration of an exemplary image used in determining distances of points on an object to fit a subject to mobility assistive equipment.

FIG. 4 is an illustration of an exemplary image 400 used in determining distances of points on an object in the image 400 to fit a subject 102 to mobility assistive equipment 104. The illustrated example of an image 400 includes a first sequence of points 402. The sequence of points 402 may include two or more points. In at least some embodiments, the I/O component 224 of the electronic device 204 receives input from a user corresponding to a selection of the sequence of points 402. Then, based on the selection of the sequence of points 402, the distance component 238 may calculate distances between adjacent points in the sequence of points 402. In at least some embodiments, the distance component may sum the distances between adjacent points to determine a distance 404 between a first point in the sequence of points 402 and the last point in the sequence of points 402. In at least some embodiments, the distance 404 may be a Euclidean distance (i.e., a straight-line distance) between the two adjacent points 402. To determine the Euclidean distance, the distance component 238 may receive the coordinates of the components of the points 402 from the sensed data 218 and calculate the distance between adjacent points 402 based on the coordinates of the points 402 using the Pythagorean Theorem and/or using another formula.

The example image 400 also includes a second sequence of points 406. In this embodiment, the sequence of points 406 may automatically be selected by the distance component 238. In at least some embodiments, the distance component 238 may automatically select the sequence points 406 based on the type of mobility assistive equipment 104 to which the subject 102 is being fitted. For example, the I/O component 224 may receive input from a user (e.g., the subject 102 and/or a third-party) as to what type of mobility assistive equipment 104 to which the subject 102 will be fitted. Then, based on the inputted type of mobility assistive equipment 104, the distance component 238 may automatically select one or more sets of sequences of points 406 that are important for fitting the subject 102 to the inputted type of mobility assistive equipment 104. The location of the selected one or more sets of points 406 may be determined based on the features identified by the feature component 236. Once the sequence of points 406 are automatically selected, the distance component 238 may then determine the distance between adjacent points in the sequence of points 406. In at least some embodiments, the distance component may sum the distances between adjacent points to determine a distance 408 between a first point in the sequence of points 406 and the last point in the sequence of points 406. In the illustrated example, the distance 408 between the outer arms of the subject 102 is determined to be important so the distance component 238 automatically selects the sequence of points 406 and determines the distance 408 between the sequence of points 406 using the coordinates in the point cloud representation.

In at least some embodiments, such as the one illustrated in FIG. 4, the distance 408 may also be a non-Euclidean distance. A non-Euclidean distance 408 may be determined by the distance component 238 in several ways. In one example, the curvature may be calculated based on the points included in the point-cloud representation. That is, the point-cloud representation includes points along a curved surface of an object (e.g., the subject 102). The distance component 238 then calculates a minimal distance between adjacent points in the sequence of points 406 as constrained to the surface of the object by, for example, performing a line integral. The distances between adjacent points in the sequence of points 406 may then be summed to determine the distance 408. In another example, the I/O component may receive a curvature to be applied between the set of points 406 and the distance component 238 may calculate the minimal distance 408 based on the received curvature. In even another example, the distance component 238 calculates the distance between two points on a surface constrained to the path defined by the intersection of a user-defined planar cross section and the surface of the image 400. As even another example, the distance component 238 calculates the distance between two points constrained to a path on the surface of the model 100% defined by the user, for example, by tracing along the surface of the image 400. As even another example, the distance component 238 calculates the distance as the sum of straight line distances on a sequence of points (e.g., the distance from the shoulder to the elbow to the wrist to the fingertip). Additionally, or alternatively, angles between lines may be determined and/or shapes for tray cutouts.

In at least some embodiments, a user (e.g., the subject 102 and/or a third-party) may select whether the distance component 238 determines a Euclidean distance or non-Euclidean distance between a set of points 402, 406. Additionally, or alternatively, whether the distance component 238 determines a Euclidean distance or non-Euclidean distance may be determined based on characteristics of the set of points 402, 406. For example, in some instances, a Euclidean distance between a specific set of points 402, 406 may be more beneficial to fitting a subject to mobility assistive equipment 104. And in other instances, a non-Euclidean distance between a different set of points 402, 406. As such, the distance component 238 may determine which type of distance is more beneficial to fitting the subject 102 to mobility assistive equipment 104 based on the specific set of points 402, 406 for which a distance is to be determined.

To determine which type of distance is more beneficial, the distance component 238 may query a lookup table having as a first field the set of points 402, 406 for which a distance therebetween is being determined. The lookup table may also have a corresponding second field that indicates what type of distance is more beneficial for the distance component 238 to calculate to fit a subject 102 to mobility assistive equipment 104. And, based on the type of distance in the second field, the distance component 238 calculates the corresponding distance.

Additionally, or alternatively, angles between lines may be determined and/or shapes for tray cutouts. For example, a sequence of points 410 may be determine in response to a user input. In addition, a first line segment 412 may be determined by extending a line between adjacent points 410A, 410B of the sequence of points 410 and a second line segment 414 may be determined by extending a line between adjacent points 410B, 410C of the sequence of points 410. An angle may then be determined between the two line segments 412, 414 by the distance component 238 by determining the slope of each line. For example, let $m_1$ be the slope for line segment 412 and $m_2$ be the slope for line segment 414. The distance component 238 may then determine the angle between the lines 412, 414 by computing the inverse tangent of $|(m1-m2)/(1+m1*m2)|$.

After calculating one or more distances between one or more sets of points 402, 406, the distance component 238 may send the calculated distance(s) to the sizing component 240 stored in memory 222 (depicted in FIG. 2). The sizing component 240 may determine an appropriately-sized mobility assistive equipment 104 for the subject 102 based on the calculated distance(s).

In at least one embodiment, the sizing component 240 may determine an appropriately-sized mobility assistive equipment 104 for the subject 102 based on the calculated distance(s) using one or more lookup tables. For example, a lookup table may include one or more fields that include different sets of points on a subject 102. For the different sets of points on the subject 102, the lookup table may include ranges of distances. Further, each range of distances may be associated with different sized mobility assistive equipment 104 and/or accessories associated therewith. As such, the sizing component 240 may receive determined distances for different sets of points from the distance component 238. In response to receiving the determined distances, the sizing component 240 may query the lookup table to determine within which ranges the determined distances are in the lookup table. Then, an appropriately sized mobility assistive equipment may be correlated to the specific ranges within which the determined distances are located. For example, the distance component 238 may have calculated distances of $a_1 \ldots a_n$ between a respective set of points $b_{11} \ldots b_{nn}$ on a subject 102 included in the image 400. Then, the sizing component 240 may determine in which ranges the calculated distances of $a_1 \ldots a_n$ are located in the lookup table. After determining within which ranges the calculated distances of $a_1 \ldots a_n$ are located, the sizing component 240 may determine a respectively sized mobility assistive equipment 104 based on a correlation between the respectively sized mobility assistive equipment 104 and the determined ranges.

Additionally, or alternatively, the sizing component 240 may determine an appropriately sized mobility assistive equipment 104 using machine learning techniques operating on a data set populated with existing fits of a subject 102 and mobility assistive equipment 104. In at least some embodiments, the sizing component 240 may output cross-sectional drawings for the appropriately-sized mobility assistive equipment 104 (e.g., tray cutouts, helmet sizing, and/or molded/custom seating).

In embodiments, a center of gravity for the subject 102 and the appropriately sized mobility assistive equipment 104 may be determined when the subject 102 is in a "home" position relative to the appropriately sized mobility assistive equipment 104. For example, a volume integral over the model of the subject 102 and the mobility assistive equipment 104 may be used to determine the center of gravity for the subject 102 and the mobility assistive equipment 104. In embodiments, a uniform density of the integrated volume can be assumed when calculating the center of gravity for the integrated volume. In another embodiment, respective uniform densities of the subject 102 and the mobility assistive equipment 104 can be assumed when calculating the center of gravity for the integrated volume. In even another embodiment, features identified by the feature component 236 and their sizes calculated based on the distances determined by the distance component 238 can be correlated to body mass tables for the identified features to estimate the densities of the identified features. Then, the center of gravity of the subject 102 and the mobility assistive equipment 104 can be determined using the identified densities.

Additionally, or alternatively, the stability of the subject 102 and the appropriately sized mobility assistive equipment 104 may be determined using the center of gravity. For example, the electronic device 204 may be determine how the center of gravity changes when the subject 102 changes his/her position relative to the mobility assistive equipment 104 from a home position to one of a plurality of other positions. In embodiments, the home position for a subject 102 in a wheelchair 104 may be with his/her arms on the armrest and another position for the subject 102 may be when his/her arm is extended forward or laterally to reach for an object. The electronic device 204 can then calculate how the center of gravity of the subject and the mobility assistive equipment 104 changes when the subject 104 transitions from the home position to the alternate position using statics methods from engineering. Further, the electronic device 204 can determine the altered center of gravity relative to the ground contact points (i.e., the wheels) of the wheelchair and determine whether the subject 102 will be stable making this movement while arranged on the mobility assistive equipment 104. In embodiments where the electronic device 204 determines the subject 102 is not stable making ordinary movements by a subject 102 while arranged on an appropriately sized mobility assistive equipment 104, the electronic device 204 may select a different mobility assistive equipment 104 that is appropriately sized and provides better stability for the subject 102.

In at least some embodiments, the electronic device 204 may also determine limitations for a slope on which the subject 102 and the mobility assistive equipment 104 can be used using the center of gravity. For example, the maximum slope on which the subject 102 and the mobility assistive equipment 104 can be used is when the center of gravity of the subject 102 and the mobility assistive equipment 104 falls outside the ground contact points of the mobility assistive equipment 104. Additionally, or alternatively, the electronic device 204 can determine the dynamic stability of the subject 102 and the mobility assistive equipment 104 by analyzing limits in acceleration and duration of acceleration that would result in the center of gravity moving outside the ground contact points of the mobility assistive equipment 204. In at least some embodiments, the electronic device 204 may determine one or more of the stability calculations above for different variations in posture of the subject 104.

Additionally, or alternatively, the electronic device 204 may determine how the center of gravity changes for a plurality of different transfer functions for the subject 102. For example, an exemplary transfer function is when the subject 102 is removed from the appropriately sized mobility assistive equipment 104. Based on the changing center of gravity, the electronic device 204 may determine the required forces, to be applied to different portions of the subject 102 and/or by the subject 102, that are required for each of the plurality of transfer functions. The electronic device 204 may output a complete force analysis, including a timeseries and min/max force numbers.

In at least some embodiments, the electronic device 204 may generate a scaled image of the subject 102 and the appropriately sized mobility assistive equipment 104 in a virtual environment to determine whether and/or how the subject 102 and the mobility assistive equipment 104 fits in the virtual environment. For example, a scaled image of the subject 102 and the mobility assistive equipment 104 may be loaded into a virtual representation of the subject's home, office, garage, gazebo, etc. to determine how the subject 102 and the mobility assistive equipment 104 fit within one or more of those spaces.

The I/O component 224 may include a user interface configured to present information to a user or receive an indication from a user. For example, the I/O component 224 may include and/or be coupled to a display device, a printing device, a light emitting diode (LED), and/or the like, and/or an input component such as, for example, a button, a joystick, a satellite dish, a scanner, a printer, a wireless device, a keyboard, a pen, a voice input device, a touch input device, a touch-screen device, an interactive display device, a mouse, and/or the like. In embodiments, the I/O component 224 may be used to present and/or provide the sensed data 218, the results of the model-fitting component 232, the orientation component 234, the distance component 238 and/or the sizing component 240, and/or any other data and/or results by the electronic device 204 and/or any other components depicted in FIGS. 1 and 2. Additionally, or alternatively, the I/O component 224 may receive a command from a subject 102 and/or third party and, in response to the command, the processor 220 may execute the command. For example, the processor 220 may instruct the results of the model-fitting component 232, the orientation component 234, the distance component 238 and/or the sizing component 240 to be sent to a server (e.g., the server 114 and/or to another electronic device (e.g., the second electronic device 116) via the communication component 226. After being sent to a server and/or another electronic device, the results of the model-fitting component 232, the orientation component 234, the distance component 238 and/or the sizing component 240 may be stored, compared to other results from subject 102 and/or other subjects, reviewed by an ATP and/or clinician, and/or receive feedback in response to the comparison and/or review via the communication component 226.

The communication component 226 may be configured to communicate (i.e., send and/or receive signals) with the sensing device 202 and/or other devices included in FIGS. 1 and 2 (e.g., the first electronic device 110, the server 114, the second electronic device 116). For example, the communication component 214 may be configured to receive sensed data 218 from the sensing device 202 and/or send the results of the model-fitting component 232, the orientation component 234, the distance component 238 and/or the sizing component 240 to another device (e.g., the first electronic device 110, the server 114, the second electronic device 116, an/or the sensing device 202). The communication component 226 may include, for example, circuits, program components, and one or more transmitters and/or receivers for communicating wirelessly with one or more other devices such as, for example, the first electronic device 110, the server 114, the second electronic device 116, an/or the sensing device 202. According to various embodiments, the communication component 226 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 226 may include any combination of hardware, software, and/or firmware configured to facilitate establishing, maintaining, and using any number of communication links.

The power source 228 provides electrical power to the other operative components of the electronic device 204, for example, the processor 220, the memory 222, the I/O component 224, and/or the communication component 226, and may be any type of power source suitable for providing the desired performance and/or longevity requirements of the electronic device 204. In various embodiments, the power source 228 may include one or more batteries, which may be rechargeable (e.g., using an external energy source). The power source 228 may include one or more capacitors, energy conversion mechanisms, and/or the like.

Due to the embodiments disclosed herein, a subject 102 may be able to be fitted to mobility assistive equipment and/or one or more accessories of mobility assistive equipment without the subject having to be in the same location as an ATP and/or clinician. Furthermore, potential issues experienced by a subject 102 may be reviewed and addressed by an ATP and/or clinician located in a different location than the subject 102.

The illustrated embodiment shown in FIG. 2 is not intended to suggest any limitation as to the scope of use or functionality of embodiments of the present disclosure. The illustrative embodiment should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are within the ambit of the subject matter disclosed herein.

Referring to FIG. 5, an illustration of a flow diagram of a method 500 for determining an orientation of an image used for fitting a subject to mobility assistive equipment. The method 500 may include receiving an image of one or more objects (block 502). In embodiments, the image and the one or more objects may have the same or similar characteristics as the image and the one or more objects discussed above in relation to the other figures. Additionally, or alternatively, the method 500 may include imaging one or more objects. In embodiments, a sensor may have the same or similar functionality as the sensing devices 108, 202 discussed above.

The method 500 may further comprise generating a plurality of subset of points in the image (block 504) and fitting a parametric model to each subset of the plurality of subsets (block 506). In embodiments, the plurality of subsets of points may be generated in the same or similar manner as discussed above and/or by the same or similar components as the components as discussed above. Additionally, or alternatively, a parametric model may be fitted to each subset of the plurality of subsets in a same or similar manner as discussed above and/or by the same or similar components as the components as discussed above.

The method 500 may further comprise identifying a parametric model of the plurality of parametric models with the largest number of points (block 508) and orienting the image based on the identified parametric model (block 510). The parametric model of the plurality of parametric models may be identified in the same or similar manner as discussed above and/or by the same or similar components as the components as discussed above. In addition, the image may be oriented based on the identified parametric model in the same or similar manner as discussed above and/or by the same or similar components as the components as discussed above.

Method 500 may further comprise calculating a distance between a sequence of at least two points on the image (block 512). In embodiments, the method 500 may include calculating a distance between adjacent points in the sequence of the at least two points on the image in the same or similar manner as discussed above and/or by the same or similar components as the components as discussed above.

In at least some embodiments, the method 500 may include fitting a user to a mobility assistive equipment and/or accessories (block 514). The method 500 may fit a user to a mobility assistive equipment and/or accessories in the same or similar manner as discussed above and/or by the same or similar components as the components as discussed above.

The method 500 may further comprise outputting to a display device: the oriented image, one or more of the calculated distances, and/or the calculated fit for a subject (block 516). Additionally, or alternatively, the oriented image, one or more of the calculated distances, and/or the calculated fit for a subject may be transmitted over a network (e.g., the network 112) to a server (e.g., the server 114) and/or another electronic device (e.g., the second electronic device 116) for storage, comparison to other results from the subject and/or other subjects, review by an ATP and/or clinician.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all the described features. Accordingly, the scope of the present disclosure is intended to embrace all such alternatives, modifications, and variations as fall within the scope of the claims, together with all equivalents thereof.

We claim:

1. A method for determining orientation of a scanned image and using the oriented image to fit a subject to mobility assistive equipment, the method comprising:
   receiving image data of a scanned image of one or more objects, wherein each object of the one or more objects in the image includes a plurality of points on a surface of the object;
   generating a plurality of subsets of points of the plurality of points;
   fitting a parametric model to more than one subset of the plurality of subsets to generate a plurality of parametric models;
   identifying a parametric model of the plurality of parametric models that includes the largest number of points;
   orientating the image based on the parametric model that includes the largest number of points; and
   fitting the subject to the mobility assistive equipment using the oriented image.

2. The method of claim 1, wherein orienting the image comprises setting the parametric model that includes the largest number of points as a ground of the image.

3. The method of claim 1, wherein fitting a parametric model to more than one subset of the plurality of subsets comprises fitting a parametric model to each subset of the plurality of subsets.

4. The method of claim 1, wherein the image comprises at least one of: the subject and mobility assistive equipment.

5. The method of claim 1, wherein the image is a scan of the one or more objects from a three-dimensional scanner.

6. The method of claim 1, further comprising outputting to a display device the oriented image.

7. The method of claim 6, further comprising:
   receiving an input sequence from an input device, the input sequence comprising a selection of a sequence of at least two points on the image; and
   determining a real-world distance by summing adjacent points of the input sequence.

8. The method of claim 7, further comprising determining an angular relationship between two adjacent segments, wherein each adjacent segment of the two adjacent segments comprises two or more adjacent points of the input sequence.

9. The method of claim 7, further comprising outputting an image of a custom component for the mobility assistive equipment based on the real-world distance.

10. The method of claim 9, wherein the custom component is at least one of: a tray cutout, a helmet sizing, and a seat.

11. The method of claim 7, further comprising determining a size of a mobility assistive equipment to fit the subject based on the real-world distance.

12. The method of claim 7, wherein the real-world distance is a Euclidean distance or a contour distance.

13. The method of claim 11, further comprising transmitting the determined size to a remote electronic device.

14. A non-transitory computer readable medium having a computer program stored thereon for determining orientation of a scanned image and using the oriented image to fit a subject to mobility assistive equipment, the computer program comprising instructions for causing one or more processors to:
- receive image data of an image of one or more objects, wherein each object of the one or more objects in the image includes a plurality of points on a surface of the object;
- generate a plurality of subsets of points of the plurality of points;
- fit a first parametric model to a first subset of the plurality of subsets;
- orient the image based on the first parametric model when a number of points on the first parametric model is greater than or equal to a threshold;
- fit a second parametric model to a second subset of the plurality of subsets when the number of points on the first parametric model is less than a threshold;
- orient the image based on the second parametric model; and
- fit the subject to the mobility assistive equipment using the oriented image.

15. The non-transitory computer readable medium of claim 14, wherein to orient the image, the computer program comprises instructions to set the first parametric model as a ground of the image.

16. The non-transitory computer readable medium of claim 14, the computer program comprising instructions to assign coordinates to each point of the plurality of points.

17. The non-transitory computer readable medium of claim 14, wherein the image comprises at least one of: the subject and mobility assistive equipment.

18. The non-transitory computer readable medium of claim 14, wherein the image is a scan of the one or more objects from a three-dimensional scanner.

19. The non-transitory computer readable medium of claim 14, the computer program comprising instructions to output to a display device the oriented image.

20. The non-transitory computer readable medium of claim 19, the computer program comprising instructions to:
- receive an input from an input device, the input comprising at least two points on the image; and
- determine a real-world distance between the two points.

21. The non-transitory computer readable medium of claim 20, the computer program comprising instructions to determine a size of a mobility assistive equipment to fit the subject based on the real-world distance.

22. The non-transitory computer readable medium of claim 20, wherein the real-world distance is a Euclidean distance or a contour distance.

23. The non-transitory computer readable medium of claim 21, the computer program comprising instructions to transmit the determined size to a remote electronic device.

* * * * *